US006534051B1

(12) United States Patent
Dornburg

(10) Patent No.: US 6,534,051 B1
(45) Date of Patent: ***Mar. 18, 2003

(54) CELL TYPE SPECIFIC GENE TRANSFER USING RETROVIRAL VECTORS CONTAINING ANTIBODY-ENVELOPE FUSION PROTEINS AND WILD-TYPE ENVELOPE FUSION PROTEINS

(75) Inventor: Ralph Dornburg, Lansdale, PA (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/135,121

(22) Filed: Aug. 17, 1998

Related U.S. Application Data

(63) Continuation-in-part of application No. 08/933,616, filed on Aug. 28, 1997, now Pat. No. 5,869,331, which is a continuation of application No. 08/205,980, filed on Mar. 4, 1994, now abandoned, which is a continuation-in-part of application No. 07/979,619, filed on Nov. 20, 1992, now abandoned.

(51) Int. Cl.$^7$ ...................... A61K 48/00; C12N 15/867; C12N 15/63
(52) U.S. Cl. .................. 424/93.2; 435/320.1; 435/69.1; 435/455; 435/456; 435/325; 435/326; 435/5; 435/6; 424/93.1; 424/93.6; 536/23.1; 536/23.5; 536/23.53
(58) Field of Search .............................. 435/320.1, 69.1, 435/455, 456, 325, 326, 5, 6; 424/93.2, 93.6, 93.1; 536/23.1, 23.5, 23.53

(56) References Cited

U.S. PATENT DOCUMENTS 5,869,331 A * 2/1999 Dornburg ................ 435/320.1
6,133,029 A * 10/2000 Gruber et al. .............. 435/366

FOREIGN PATENT DOCUMENTS

| WO | WO 90 12087 A | 10/1990 |
|---|---|---|
| WO | WO 92/05266 | 4/1992 |
| WO | WO 92 06180 A | 4/1992 |
| WO | WO 93 00103 | 1/1993 |
| WO | WO 94 06920 | 3/1994 |
| WO | WO 94 12626 A | 6/1994 |
| WO | WO 95/23846 | 9/1995 |

OTHER PUBLICATIONS

Marshall, "Gene Therapy's Growing Pains," *Science* vol. 269, Aug. 25, 1995, pp. 1050–1055.
Morgan, et al. "Human Gene Therapy," *Annual Rev. Bunhem.* vol. 62 (1991) 217, pp. 191–217.
Weiss, et al. (Ed.) "RNA Tumor Viruses," Cold Spring Harbor Laboratory (1984) pp. 46–51 and 226–260.
Te–Hua, et al., "Toward Highly Efficient Cell–Type–Specific Gene Transfer with Retroviral Vectors Displaying Single–Chain Antibodies," Journal of Virology, vol. 71, 1997, pp. 720–725.
Te–Hua, et al., "Retroviral Vector Particles Displaying the Antigen–Binding Site of an Antibody Enable Cell–Type–Specific Gene Transfer," Journal of Virology, vol. 69 [1], 1995, pp. 2659–2663.
Kewalramani, V.N., et al. "Spleen Necrosis Virus, an avian innunossupressive retrovirus, shares a receptor with the type D simian retroviruses", *Journal of Virology*, vol. 66, No. 5, May 1992, pp. 3026–3031.
Riley, S.C., et al. "Preferential expression of variable region heavy chain gene segments by predominant 2,4–dinitrophenyl–specific BALB/c neonatal antibody clonotypes," *Proceedings of the National Academy of Sciences of USA*, vol. 83, No. 8, Apr. 1986, pp. 2589–2593.
Russell, S.J. et al. "Retroviral vectors displaying functional antibody fragments," *Nucleic Acids Res.* (1993), 21(5), pp. 1081–1085.
Te–Hua, T.C., et al. "Cell targeting with retroviral vector particles containing antibody–envelope fusion proteins," *Gene Therapy*, vol. 1, No. 5, Sep. 1994, pp. 292–299.
Orkin et al., "Report and Recommendations of the Panel to Asses the NIH Investment in Research on Gene Therapy," Dec. 7, 1995.
Vera et al., *Nature*, vol. 389, pp. 239–242, Sep. 18, 1997.

* cited by examiner

*Primary Examiner*—David Guzo
(74) *Attorney, Agent, or Firm*—Senniger, Powers, Leavitt & Roedel

(57) ABSTRACT

A method of infecting target cells with retroviral vector particles having target cell specificity. The retroviral vector particles have a chimeric envelope protein consisting of an antigen binding site of an antibody or another peptide, fused to the envelope protein the retroviral vector. The antigen binding site or other peptide disrupts the natural viral receptor binding site. The method includes producing the retroviral vector and contacting the vector with the target cell such that the vector is internalized by the cell.

**15 Claims, 11 Dr pSNV-env-mC pSNV-env-mD pTC4 pTC5 pJD214 HV

FIG. 3

```
ACTGGAGGCT GATTTTGAA  GAAAGGGGTT GTAGCCTAAA AGATGATGGT
GTTAAGTCTT CTGTACCTGT TGACAGCCCT TCCGGGTATC CTGTCAGAGG
TGCAGCTTCA GGAGTCAGGA CCTAGCCCTG TGAAACCTTC TCTGACTCTG
TCCCTCACCT GTTCTGTCAC TGGCGACTCC ATCACCAGTG GTTACTGGAA
CTGGATCCGG AAATTCCCAG GGAATAAACT TGAGTACATG GGGTACATAA
GCTACAGTGG TAGCACTTAC TACAATCCAT CTCTCAAAAG TCGAATCTCC
ATCACTCGAG ACACATCCAA GAACCAGTAC TACCTGCAGT TGAATTCTGT
GACTACTGAG GACACAGCCA CATATTACTG TGCAAGATAT GGTGGTAACT
ATGCTATGGA GTACTGGGGT CAAGAACCT  CAGTCACCGT CTCCTCAGGA
GGTGGCGGTA CAGGTGGCGG AGGTACAGGC GGAGGTGGTA GAATTGTGAT
GACACAGTCT CCATCCTCCC TGGCTATGTC AGTAGGACAG AAGGTCACTA
TGAGCTGCAA GTCCAGTCAG AGCCTTTTAA ATAGTAGCAA TCAAAAGAAC
TATTTGGCCT GGTACCAGGA GAAACCAGGA CAGTCTCCTA AACTTCTGTT
ATACTTTGCA TCCACTAGGG AATCTGGGGT CCCTGATCGC TTCATAGGCA
GTGGATCTGG ACAGATTTC  ACTCTTACCA TCAGCAGTGT GCAGGCTGAA
GACCTGGCAG ATTACTTCTG TCAGCAACAT TATAGCACTC CGTGGACGTT
CGGTGGAGGC ACCAAGCTGG AAATCAAACG GGCTGA
```

FIG. 5

```
                            SacI           SacII
                         GAGCTCCACCGGGTAAAGGTCGTGGGAAGAC
MLV-Pro...
CCCGTGGATCCACCACTCTCGACTCAAGAAAGCTCCTGACAACCAAGAAGA
ATGGACTGTCTCACCAACCTCCGATCCGAGGGTAAAGTTGACCAGGCG
 Met AspCysLeuThrAsnLeuArgSerAlaGluGlyLysValAspGlnAla
AGCAAAATCCTAATTCTCCTTGTGGCTTGGGTGGGGGTTTGGGACCACTGCC
SerLysIleLeuIleLeuLeuValAlaTrpGlyGlyPheGlyThrThrAla
       NruI      StuI    AflII
GAAGTTTCGCGAAGGCCTTAAGTGACTAGGTACC
GluValSerArgArgPro    Stop
                                         KpnI
```

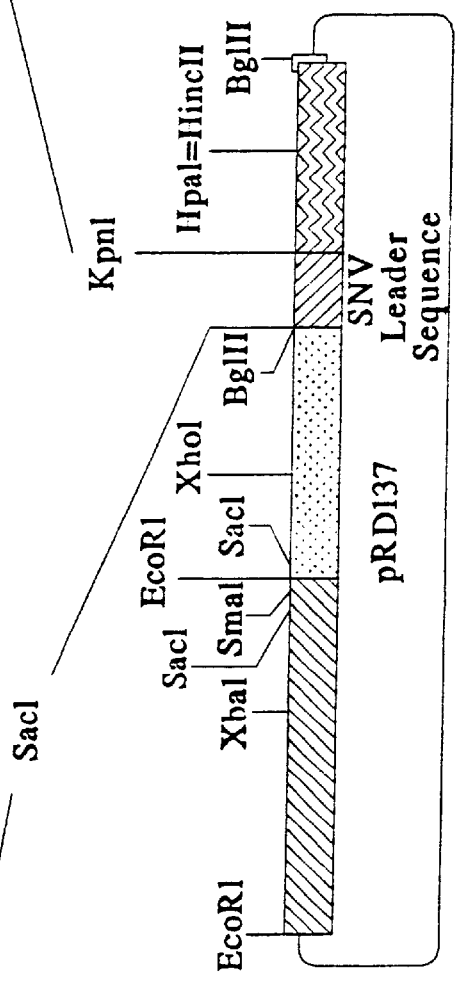

FIG. 8A

```
            10                  20                  30                  40
             *                   *                   *                   *
GCATCTACGT ACC ATG GAT TTT CAG GTG CAG ATT TTC AGC TTC CTG
            M   D   F   Q   V   Q   I   F   S   F   L>

50                  60                  70                  80                  90
         *                   *                   *                   *                   *
CTA ATC AGT GCC TCA GTC ATA ATG TCT AGA GGA GAT ATT GTG ATG
 L   I   S   A   S   V   I   M   S   R   G   D   I   V   M>

100                 110                 120                 130
             *                   *                   *                   *
ACC CAG TCT CCA AAA TTC ATG TCC ACA TCA GTA GGA GAC AGG ATC
 T   Q   S   P   K   F   M   S   T   S   V   G   D   R   I>

140                 150                 160                 170                 180
         *                   *                   *                   *                   *
AGC GTC ACC TGC AAG GCC AGT CAA GAT GTG GGT CCT AAT GTA GCC
 S   V   T   C   K   A   S   Q   D   V   G   P   N   V   A>

190                 200                 210                 220
             *                   *                   *                   *
TGG TAT CAA CAG AAA CCA GGG CAA TCT CCT AAA CCA CTG ATT TAC
 W   Y   Q   Q   K   P   G   Q   S   P   K   P   L   I   Y>

230                 240                 250                 260                 270
         *                   *                   *                   *                   *
TCG GCA TCC TAC CTA TAT AAT GGA GTC CCT GAT CGC TTC ACA GGC
 S   A   S   Y   L   Y   N   G   V   P   D   R   F   T   G>

280                 290                 300                 310
             *                   *                   *                   *
AGT GGA TCT GGG ACA GAT TTC TCT CTC ACC ATC AGC AAT GTG CAG
 S   G   S   G   T   D   F   S   L   T   I   S   N   V   Q>

320                 330                 340                 350                 360
         *                   *                   *                   *                   *
TCT GAT GAC TTG GCA GAG TAT TTC TGT CAG CAA TAT AAC ACC TAT
 S   D   D   L   A   E   Y   F   C   Q   Q   Y   N   T   Y>

370                 380                 390                 400
             *                   *                   *                   *
CCG TTC ACG TTC GGA GGG GGC ACC AAG CTG GAA ATC AAA GGG
 P   F   T   F   G   G   G   T   K   L   E   I   K   G>

410                 420                 430                 440
             *                   *                   *                   *
TCG ACT TCC GGT AGC GGC AAA TCC TCT GAA GGC AAA GGT GAG
 S   T   S   G   S   G   K   S   S   E   G   K   G   E>

450                 460                 470                 480
             *                   *                   *                   *
GTG CAG CTG GAG GAG TCT GGT GGA GGA TTG GTG CAG CCT
 V   Q   L   E   E   S   G   G   G   L   V   Q   P>
```

FIG. 8B

```
    490              500              510              520
     *                *                *                *
AAA GGG TCA TTG AAA CTC TCA TGT GCA GCC TCT GGA TTC ACC TTC
 K   G   S   L   K   L   S   C   A   A   S   G   F   T   F>

530         540         550              560         570
 *           *           *                *           *
AAT ACC TAC GCC ATG AAC TGG GTC CGC CAG GCT CCA GGA AAG GGT
 N   T   Y   A   M   N   W   V   R   Q   A   P   G   K   G>

580         590         600              610
     *           *           *                *
TTG GAA TGG ATT GTT CGC ATA AGA AGT AAA AGT AAT AAT TAT GCA
 L   E   W   I   V   R   I   R   S   K   S   N   N   Y   A>

620         630         640              650         660
 *           *           *                *           *
ACA TAT TAT GTC GAT TCA GTG AAA GAC AGG TTC ACC ATC TCC AGA
 T   Y   Y   V   D   S   V   K   D   R   F   T   I   S   R>

670         680         690         700
          *           *           *           *
GAT GAT TCA CAA AGC ATG CTC TAT CTG CAA ATG AAC AAC TTG AAA
 D   D   S   Q   S   M   L   Y   L   Q   M   N   N   L   K>

710         720         730         740         750
 *           *           *           *           *
ACT GAG GAC ACA GCC ATG TAT TAC TGT GTG ACT TCT TAC TAT GAT
 T   E   D   T   A   M   Y   Y   C   V   T   S   Y   Y   D>

760         770         780         790
          *           *           *           *
TAC GAC AAG GTC CTG TTT GCT TAC TGG GGC CAA GGG ACC ACG GTC
 Y   D   K   V   L   F   A   Y   W   G   Q   G   T   T   V>

800         810         820         830         840
 *           *           *           *           *
ACC GTC TCT TCA GCG GAT CCT CAG CTC TGC TAT ATC CTG GAT GCC
 T   V   S   S   A   D   P   Q   L   C   Y   I   L   D   A>

850         860         870         880
     *           *           *           *
ATC CTG TTT CTG TAT GGA ATT GTC CTC ACC CTC CTC TAC TGT CGA
 I   L   F   L   Y   G   I   V   L   T   L   L   Y   C   R>

890         900         910
     *           *           *
CTG AAG ATC CAA GTG CGA AAG GCA GCT
 L   K   I   Q   V   R   K   A   A>
```

FIG. 8C 920 930 940 950 960
ATA ACC AGC TAT GAG AAA TCA GAT GGT GTT TAC ACG GGC CTG AGC ACC
I T S Y E K S D G V Y T G L S T>
___a____a_____a___TRANSLATION OF N29 IN RSVGAMMA [A] _____a____a____a___>

970 980 990 1000 1110
AGG AAC CAG GAG ACT TAC GAG ACT CTG AAG CAT GAG AAA CCA CCA CAG
R N Q E T Y E T L K H E K P P Q>

1020 1030 1040 1050 1060 1070
TAG CTTTA GACTCGAGTA GATCCAGACA TGATAAGATA CATTGATGAG TTTGGACAAA
*>
___>

CCACAACTA

SEQUENCE LISTING

<160> NUMBER OF SEQ ID NOS: 7

<210> SEQ ID NO 1
<211> LENGTH: 28
<212> TYPE: DNA
<213> ORGANISM: Artificial sequence
<220> FEATURE:
<223> OTHER INFORMATION: Primer A used for PCR amplification of B6.2 scA
      gene

<400> SEQUENCE: 1 ggagcgctgacgtcgtgatgacccagtc                                         28

<210> SEQ ID NO 2
<211> LENGTH: 37
<212> TYPE: DNA
<213> ORGANISM: Artificial sequence
<220> FEATURE:
<223> OTHER INFORMATION: Primer B used for PCR amplification of B6.2 scA
      gene

<400> SEQUENCE: 2 cctcgcgatccaccgccggagactgtgagagtggtgc                                37

<210> SEQ ID NO 3
<211> LENGTH: 836
<212> TYPE: DNA
<213> ORGANISM: Artificial sequence
<220> FEATURE:
<223> OTHER INFORMATION: B6.2 gene encoding single chain antibody
      against hapten DNP

<400> SEQUENCE: 3

| actggaggct | gattttgaa  | gaaagggtt  | gtagcctaaa | agatgatggt |  50 |
| gttaagtctt | ctgtacctgt | tgacagccct | tccgggtatc | ctgtcagagg | 100 |
| tgcagcttca | ggagtcagga | cctagcctcg | tgaaaccttc | tctgactctg | 150 |
| tccctcacct | gttctgtcac | tggcgactcc | atcaccagtg | gttactggaa | 200 |
| ctggatccgg | aaattcccag | ggaataaact | tgagtacatg | gggtacataa | 250 |
| gctacagtgg | tagcacttac | tacaatccat | ctctcaaaag | tcgaatctcc | 300 |
| atcactcgag | acacatccaa | gaaccagtac | tacctgcagt | tgaattctgt | 350 |
| gactactgag | gacacagcca | catattactg | tgcaagatat | ggtggtaact | 400 |
| atgctatgga | gtactggggt | caaggaacct | cagtcaccgt | ctcctcagga | 450 |
| ggtggcggta | caggtggcgg | aggtacaggc | ggaggtggta | gaattgtgat | 500 |
| gacacagtct | ccatcctccc | tggctatgtc | agtaggacag | aaggtcacta | 550 |
| tgagctgcaa | gtccagtcag | agcctttaa  | atagtagcaa | tcaaaagaac | 600 |
| tatttggcct | ggtaccagca | gaaaccagga | cagtctccta | aacttctggt | 650 |
| atactttgca | tccactaggg | aatctggggt | ccctgatcgc | ttcataggca | 700 |
| gtggatctgg | gacagatttc | actcttacca | tcagcagtgt | gcaggctgaa | 750 |
| gacctggcag | attacttctg | tcagcaacat | tatagcactc | cgtggacgtt | 800 |
| cggtggaggc | accaagctgg | aaatcaaacg | ggctga     |            | 836 |

<210> SEQ ID NO 4
<211> LENGTH: 220
<212> TYPE: DNA

```
<213> ORGANISM: Artificial sequence
<220> FEATURE:
<223> OTHER INFORMATION: pTC13 eucaryotic gene expression vector

<400> SEQUENCE: 4
gagctccacc gcggtaaagg tcgctgggaa gaccccgtgg atccaccact          50
ctcgactcaa gaaagctcct gacaaccaag aaga                          84 atg gac tgt ctc acc aac ctc cga tcc gct gag ggt aaa gtt       126 gac cag gcg agc aaa atc cta att ctc ctt gtg gct tgg tgg       168 ggg ttt ggg acc act gcc gaa gtt tcg cga agg cct               204 taagtgacta ggtacc                                              220

<210> SEQ ID NO 5
<211> LENGTH: 40
<212> TYPE: PRT
<213> ORGANISM: Unknown
<220> FEATURE:
<223> OTHER INFORMATION: ER recognition signal sequence

<400> SEQUENCE: 5

Met Asp Cys Leu Thr Asn Leu Arg Ser Ala Glu Gly Lys Val Asp Gln Ala
 1               5                  10                  15

Ser Lys Ile Leu Ile Leu Leu Val Ala Trp Trp Gly Phe Gly Thr Thr Ala
            20                  25                  30

Glu Val Ser Arg Arg Pro
         35              40

<210> SEQ ID NO 6
<211> LENGTH: 1079
<212> TYPE: DNA
<213> ORGANISM: Unknown
<220> FEATURE:
<223> OTHER INFORMATION: DNA encoding anti-Her2neu single chain antibody

<400> SEQUENCE: 6
ggatctacgt acc atg gat ttt cag gtg cag att ttc agc ttc ctg cta atc    52 agt gcc tca gtc ata atg tct aga gga gat att gtg atg acc cag tct     100 cca aaa ttc atg tcc aca tca gta gga gac agg atc agc gtc acc tgc     148 aag gcc agt caa gat gtg ggt cct aat gta gcc tgg tat caa cag aaa     196 cca ggg caa tct cct aaa cca ctg att tac tcg gca tcc tac cta tat     244 aat gga gtc cct gat cgc ttc aca ggc agt gga tct ggg aca gat ttc     292 tct ctc acc atc agc aat gtg cag tct gat gac ttg gca gag tat ttc     340 tgt cag caa tat aac acc tat ccg ttc acg ttc gga ggg ggc acc aag     388 ctg gaa atc aaa ggg tcg act tcc ggt agc ggc aaa tcc tct gaa ggc     436 aaa ggt gag gtg cag ctg gag gag tct ggt gga gga ttg gtg cag cct     484 aaa ggg tca ttg aaa ctc tca tgt gca gcc tct gga ttc acc ttc aat     532 acc tac gcc atg aac tgg gtc cgc cag gct cca gga aag ggt ttg gaa     580 tgg att gtt cgc ata aga agt aaa agt aat aat tat gca aca tat tat     628 gtc gat tca gtg aaa gac agg ttc acc atc tcc aga gat gat tca caa     676 agc atg ctc tat ctg caa atg aac aac ttg aaa act gag gac aca gcc     724 atg tat tac tgt gtg act tct tac tat gat tac gac aag gtc ctg ttt     772
```

-continued

```
gct tac tgg ggc caa ggg acc acg gtc acc gtc tct tca gcg gat cct    820 cag ctc tgc tat atc ctg gat gcc atc ctg ttt ctg tat gga att gtc    868 ctc acc ctc ctc tac tgt cga ctg aag atc caa gtg cga aag gca gct    916 ata acc agc tat gag aaa tca gat ggt gtt tac acg ggc ctg agc acc    964 agg aac cag gag act tac gag act ctg aag cat gag aaa cca cca cag    1012 tag ctttagactc gagtagatcc agacatgata agatacattg atgagtttgg          1065
acaaaccaca acta                                                     1079
```

<210> SEQ ID NO 7
<211> LENGTH: 332
<212> TYPE: PRT
<213> ORGANISM: Unknown
<220> FEATURE:
<223> OTHER INFORMATION: Anti-Her2neu single chain antibody

<400> SEQUENCE: 7

```
Ala Asp Phe Gln Val Gln Ile Phe Ser Phe Leu Leu Ile Ser Ala Ser
 1               5                  10                  15

Val Ile Ala Ser Arg Gly Asp Ile Val Ala Thr Gln Ser Pro Lys Phe
             20                  25                  30

Ala Ser Thr Ser Val Gly Asp Arg Ile Ser Val Thr Cys Lys Ala Ser
         35                  40                  45

Asp Val Gly Pro Asn Val Ala Trp Tyr Gln Gln Lys Pro Gly Gln Ser
     50                  55                  60

Pro Lys Pro Leu Ile Tyr Ser Ala Ser Tyr Leu Tyr Asn Gly Val Pro
 65                  70                  75                  80

Asp Arg Phe Thr Gly Ser Gly Ser Gly Thr Asp Phe Ser Leu Thr Ile
                 85                  90                  95

Ser Asn Val Gln Ser Asp Asp Leu Ala Glu Tyr Phe Cys Gln Gln Tyr
            100                 105                 110

Asn Thr Tyr Pro Phe Thr Phe Gly Gly Gly Thr Lys Leu Glu Ile Lys
        115                 120                 125

Gly Ser Thr Ser Gly Ser Gly Lys Ser Ser Glu Gly Lys Gly Glu Val
    130                 135                 140

Gln Leu Glu Glu Ser Gly Gly Gly Leu Val Gln Pro Lys Gly Ser Leu
145                 150                 155                 160

Lys Leu Ser Cys Ala Ala Ser Gly Phe Thr Phe Asn Thr Tyr Ala Ala
                165                 170                 175

Asn Trp Val Arg Gln Ala Pro Gly Lys Gly Leu Glu Trp Ile Val Arg
            180                 185                 190

Ile Arg Ser Lys Ser Asn Asn Tyr Ala Thr Tyr Tyr Val Asp Ser Val
        195                 200                 205

Lys Asp Arg Phe Thr Ile Ser Arg Asp Asp Ser Gln Ser Ala Leu Tyr
    210                 215                 220

Leu Gln Ala Asn Asn Leu Lys Thr Glu Asp Thr Ala Ala Tyr Tyr Cys
225                 230                 235                 240

Val Thr Ser Tyr Tyr Asp Tyr Asp Lys Val Leu Phe Ala Tyr Trp Gly
                245                 250                 255

Gln Gly Thr Thr Val Thr Val Ser Ser Ala Asp Pro Gln Leu Cys Tyr
            260                 265                 270

Ile Leu Asp Ala Ile Leu Phe Leu Tyr Gly Ile Val Leu Thr Leu Leu
        275                 280                 285
```

```
                                         -continued

Tyr Cys Arg Leu Lys Ile Gln Val Arg Lys Ala Ala Ile Thr Ser Tyr
        290                 295                 300

Glu Lys Ser Asp Gly Val Tyr Thr Gly Leu Ser Thr Arg Asn Gln Glu
305                 310                 315                 320

Thr Tyr Glu Thr Leu Lys His Glu Lys Pro Pro Gln
                325                 330
```

CELL TYPE SPECIFIC GENE TRANSFER USING RETROVIRAL VECTORS CONTAINING ANTIBODY-ENVELOPE FUSION PROTEINS AND WILD-TYPE ENVELOPE FUSION PROTEINS

This application is a continuation-in-part of application Ser. No. 08/933,616 filed Aug. 28, 1997, now U.S. Pat. No. 5,869,331, which is continuation of application Ser. No. 08/205,980, filed Mar. 4, 1994, now abandoned, which is a continuation-in-part of application Ser. No. 07/979,619, filed Nov. 20, 1992 now abandonded.

BACKGROUND OF THE INVENTION

1. Field of the Invention

This invention relates to retroviral vector particles having target cell specificity. The retroviral vector particles comprise a retroviral vector having a chimeric envelope protein consisting of an antigen binding site of an antibody or another peptide fused to the envelope protein of the retroviral vector. The antigen binding site or the other peptide replaces or disrupts the natural viral receptor binding site. The resulting chimeric envelope is referred to as the "targeting envelope". This invention relates to retroviral vectors that contain not only the targeting envelope but also wild-type envelope protein. The presence of wild-type envelope in addition to the targeting envelope acts as a helper molecule by supplying a fully functional membrane fusion domain, which may be impaired in targeting envelopes. This helper function enables and/or enhances infection of cells that do not contain a receptor for the wild-type envelope but do contain a receptor for the binding for the targeting molecule. This invention also relates to a method for preparing the retroviral particles and for using the retroviral vectors to introduce genes into vertebrate cells.

2. Description of the Background

The disclosures referred to herein to illustrate the background of the invention and to provide additional detail with respect to its practice are incorporated herein by reference. For convenience, the disclosures are referenced in the following text and respectively grouped in the appended bibliography.

Retroviral vectors are the most efficient tools to introduce genes into vertebrate cells. Clinical experiments have been conducted to use retrovirus vectors to cure a genetic disease in humans (adenosine deaminase (ADA) deficiency). Besides correcting inborn errors of metabolism, gene therapy is also being tested in clinical trials to cure cancer and various other diseases (Science 1992, Vol. 258, pp. 744–746).

Retroviral vectors are basically retroviral particles that contain a genome in which all viral protein coding sequences have been replaced with the gene(s) of interest. As a result, such viruses cannot further replicate after one round of infection. Retroviral vector particles are produced by helper cells (FIG. 1). Such helper cells are cell lines that contain plasmid constructs, which express all retroviral proteins necessary for replication. After transfection of the vector genome into such helper cells, the vector genome is encapsidated into virus particles (due the presence of specific encapsidation sequences). Virus particles are released from the helper cell carrying a genome containing only the gene(s) of interest (FIG. 1). In the last decade, several retroviral vector systems derived from chicken or murine retroviruses, have been developed for the expression of various genes (for reviews see Temin, 1987; Gilboa, 1990).

Retroviral vectors have several limitations. Besides the limited genome size that can be encapsidated into viral particles, the most limiting factor for the application of retroviral vectors is the restricted host range of the vector particle. Some retroviruses can only infect cells of one species (ecotropic retroviruses) or even only one cell-type of one species (e.g., HIV). Other retroviruses have a very broad host range and can infect many different types of tissues of many different species (amphotropic retroviruses).

The initial step of retroviral infection is the binding of the viral envelope (env) glycoprotein to specific cell membrane receptors, the nature of which is unknown for most retroviruses. However, the interaction of the viral env protein with the cell surface receptor is very specific and determines cell-type specificity of a particular virus (Weiss et al., 1985). The envelope protein of all known retroviruses is made up of two associated peptides, (e.g., gp70 and p20(E) in SNV). These peptides are derived by proteolytic cleavage from the same precursor (gPR90env) encoded by the retroviral env gene. One peptide p20(E), also termed TM, anchors the protein in the membrane of the virus and, as shown with HIV, mediates the fusion of the virus and cell membranes. The second peptide gp70, also termed SU, mediates the binding of the virus to its receptor and, therefore, determines the host range (Weiss et al., 1985; Varmus and Brown, 1989).

Data obtained with several retroviruses indicate that the retroviral envelope protein forms trimers or tetramers. The formation of trimers appears to be mediated by the TM peptide (reviewed in Hunter, E. et al., 1990). Targeting envelopes retain TM in order to (i.) maintain a membrane fusion function and (ii) maintain oligomerization. However, since X-ray pictures are not available, it is unclear whether or to what degree the construction of targeting-molecules impaired the structure of the membrane fusion domain.

BRIEF DESCRIPTION OF THE FIGURES

FIG. 3 shows the sequence (SEQ ID NO:3) of the single chain antibody gene (scFv) against the hapten DNP.

FIG. 5 is a diagram (SEQ ID NOS:4 and 5) of a eucaryotic gene expression vector construct. The gene expression vector was derived from a similar vector described by Sheay, W. et al., 1993.

FIG. 8 (Parts A–C) shows the sequence (SEQ ID NOS:6 and 7) of the anti-Her2neu single chain antibody.

SUMMARY OF THE INVENTION

The present invention pertains to a retroviral vector particle having defined target cell specificity mediated by the nature of the targeting envelope which can be a chimeric protein consisting of an antigen binding site of an antibody or another peptide that binds to a specific cell surface structure (e.g., the receptor binding domain of another virus) fused to carboxy terminal parts of the retroviral envelope protein. The targeting envelope mediates the first step of retroviral infection, which is the binding of the virus to a specific cell-surface receptor. The present invention also pertains to retroviral particles that contain a wild-type envelope in addition to the targeting envelope. The presence of the wild-type envelope serves to act as a helper molecule to improve or supplement a functional membrane fusion domain. Using target cells that do not contain a receptor for the wild-type envelope (e.g., SNV is not infectious for human cells), the wild-type envelope is only involved in the second step of retroviral infection, which is the efficient fusion of the viral and the cellular membranes. The present invention also pertains to the construction of retroviral vectors particles containing a wild-type envelope in addition to a targeting envelope which can compensate for the loss of infectivity observed with retroviral particles that contain targeting envelopes alone.

In one embodiment, the present invention pertains to a retroviral vector particle having target cell specificity which comprises a retroviral vector having a targeting peptide fused to the envelope protein of the retroviral vector to form a targeting envelope, wherein the targeting peptide replaces or disrupts the natural viral receptor binding site and the targeting peptide is the antigen binding site of an antibody, the receptor binding peptide of another virus, or is a peptide that specifically binds to a specific receptor of the target.

In another embodiment, the present invention pertains to a cell type specific method for introducing genes into vertebrate cells using retroviral vectors which comprises administering to the cells a retroviral vector particle having target cell specificity which comprises a retroviral vector having a targeting peptide fused to the envelope protein of the retroviral vector to form a targeting envelope, wherein the targeting peptide replaces or disrupts the natural viral receptor binding site and the targeting peptide is the antigen binding site of an antibody, the receptor binding peptide of another virus, or is a peptide that specifically binds to a specific receptor of the target.

In yet another embodiment, the present invention pertains to a method for preparing a retroviral vector particle having target cell specificity which comprises a retroviral vector having a targeting peptide fused to the envelope protein of the retroviral vector to form a targeting envelope, wherein the targeting peptide replaces or disrupts the natural viral receptor binding site and the targeting peptide is the antigen binding site of an antibody, the receptor binding peptide of another virus, or is a peptide that specifically binds to a specific receptor of the target, which comprises the steps of:

(a) providing a targeting peptide;

(b) replacing part of the envelope gene coding for the viral receptor binding site with the targeting peptide to form a chimeric envelope gene;

(c) cloning the chimeric envelope gene in a eucaryotic gene expression vector; and (d) transfecting the chimeric envelope expression plasmid, a retroviral core protein expression plasmid, and a selectable marker gene expression plasmids into eucaryotic cells.

DETAILED DESCRIPTION OF THE INVENTION

Targeting Envelope

This invention relates to retroviral vector particles having target cell specificity. The retroviral vector particles comprise a retroviral vector having a chimeric envelope protein consisting of an antigen binding site of an antibody or another peptide fused to the envelope protein of the retroviral vector. The antigen binding site or the other peptide replaces or disrupts the natural viral receptor binding site. The resulting chimeric envelope is referred to as the "targeting envelope". This invention relates to retroviral vectors that contain not only the targeting envelope but also wild-type envelope protein. The presence of wild-type envelope in addition to the targeting envelope acts as a helper molecule by supplying a fully functional membrane fusion domain which may be impaired in targeting envelopes. This helper function enables and/or enhances infection of cells that do not contain a receptor for the wild-type envelope but do contain a receptor for the binding of the targeting molecule. This invention also relates to a method for preparing the retroviral particles and for using the retroviral vectors to introduce genes into vertebrate cells.

To alter the host range of a vector particle, retroviral vector particles may be constructed that contain modified envelope proteins that recognize only a cell surface structure (receptor) specific for the target cell of interest. Proteins known to recognize specific structures of proteins are antibody molecules. Hence, to make a retroviral vector particle specific for a cell-type of interest, the viral receptor binding peptide may be replaced with an antigen binding site of an antibody molecule. To test whether vector particles containing such antigen binding sites are competent for infection, model systems were developed using an antigen binding peptide of an antibody against the hapten dinitrophenol (DNP) fused to envelope gene of spleen necrosis virus (SNV).

The use of the anti-hapten (anti-DNP) antibody has many advantages. (1) The interaction of this antigen with the antibody is well characterized (Davies and Metzger, 1983). (2) The hapten is easily available. (3) A large variety of cells (which cannot be infected with wild-type vector particles) can be conjugated with this hapten. DNP conjugated cells bind antibodies directed against this hapten. Thus, the hapten may mimic the (abundant) presence of a receptor for the chimeric vector particle. (4) Anti-hapten antibodies are frequently internalized by the cell. Thus, the construction of chimeric envelope proteins will destroy the membrane fusion domain of TM. This property may compensate for this loss of function. (5) An in vitro binding assay can be easily established to test for virus particle formation and binding of such viruses to DNP. (6)

Wild-Type Envelope

This invention relates to retroviral particles having a target cell specificity. The retroviral vector particles comprise a retroviral vector having a targeting envelope which mediates the binding of the retroviral vector particle to a cell surface receptor of the target cell. This binding is very specific and determines the host range and cell-type specificity. The particles also have a wild type envelope. Using target cells that do not contain a viable receptor for the wild type envelope, the function of the wild-type envelope is only to supply a fully functional membrane fusion domain. This invention also relates to the method for preparing the retroviral vector particles and a method for using the retroviral vectors to introduce genes into vertebrate cells.

Retroviral vectors derived from spleen necrosis virus containing wild-type envelope alone cannot infect human or hamster cells. In these infectivity studies, retroviral particles harvested from DSN cells were used (Dougherty, J. P. and Temin, H. M. 1989) to infect human HeLa and Col-1, as well as hamster CHTG (ret. 1) cells (Tables 1 and 2). DSN cells are standard retroviral packaging cells containing a plasmid expressing the retroviral core proteins and another plasmid expressing wild-type envelope (Dougherty, J. P. and Temin, H. M. 1989).

To introduce genes into such cells using SNV retroviral vector particles, two different approaches were made using different targeting envelopes in combination with and without additional wild-type envelope.

Figure 4A:
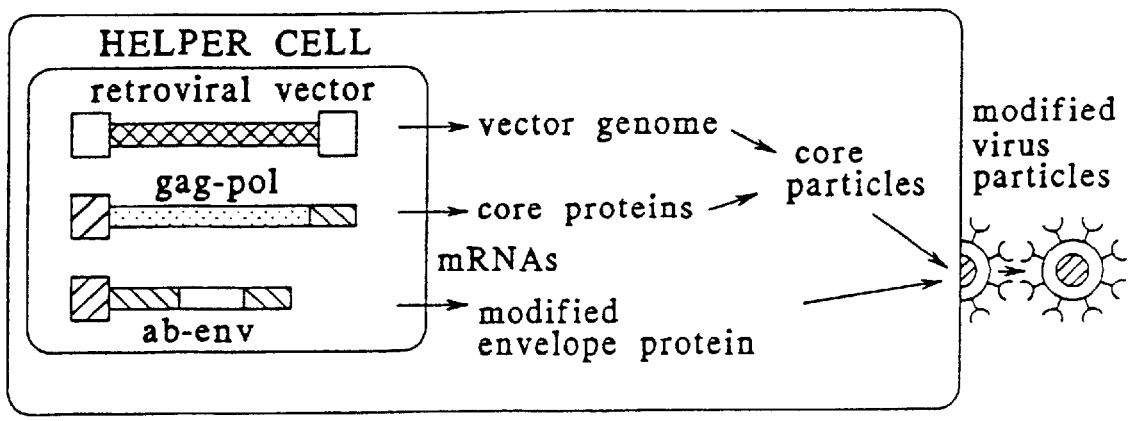
FIG. 4 (Parts A–B) is a diagram illustrating helper cells expressing targeting envelopes plus wild-type envelopes. Such helper cells are made by the transfection of plasmids expressing the corresponding proteins: (A) A helper cell expressing all retroviral proteins necessary to form (1) retroviral core proteins and (2) targeting envelope; (B) Helper cells that contain targeting plus wild-type envelope are made by transfecting plasmids expressing genes encoding such proteins. After transfection of the retroviral vector that has the gene of interest, the retroviral vector RNA genome is encapsidated into retroviral vector particles displaying the envelope.
Figure 4B:
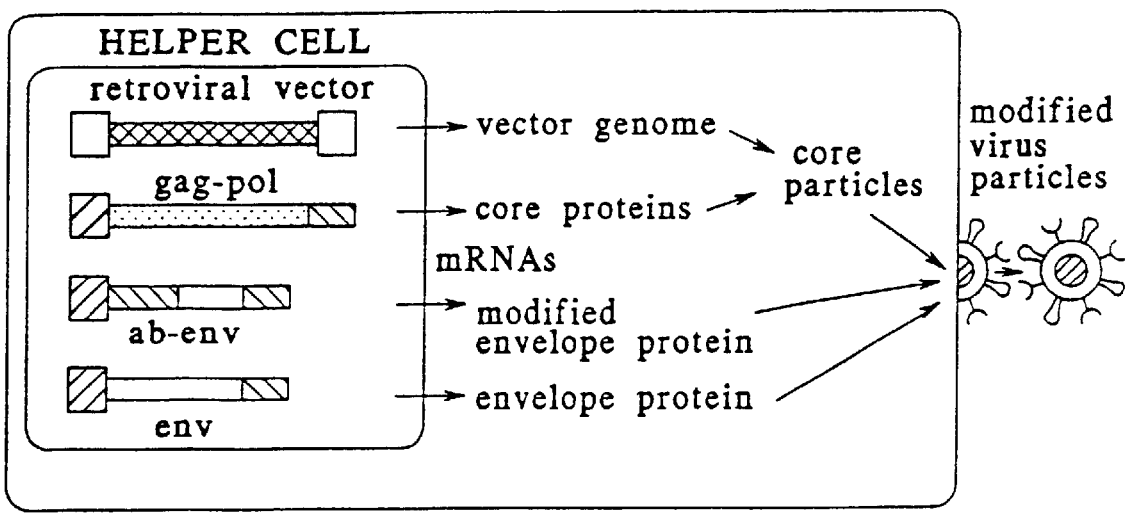

1. Targeting of human cancer cells (HeLa and Col-1) with SNV retroviral vectors. The antigen binding site of an antibody directed against the hapten DNP was used. In the experiments described below, the antigen binding site used in the targeting envelope was derived from an antibody (termed B6.2, Bird, R. E. et al., 1988 and Colcher, D. et al., 1990) directed against a cell-surface protein expressed on various human cancers (e.g., HeLa and Col-1 cells, Bird, R. E. et al., 1988 and Colcher, D. et al., 1990). The gene constructs (FIG. 6) for the expression of the targeting envelope are similar to that described above. In particular, in two constructs (FIG. 6, pTC24 and pTC25), the antibody moiety was fused to the same position of the SNV envelope gene as the anti-DNP antibody described below (for more details, see below: Material and Methods). To test whether the addition of a fully functional membrane fusion domain (provided by wild-type envelope) would increase the efficiency of infection, helper cells expressing retroviral core proteins, wild-type envelope, and the targeting envelope were developed (FIG. 4). Virus was harvested from such helper cells and subjected to infectivity studies.

2. Targeting CHTG cells that express a receptor for ecotropic murine leukemia virus. To test whether retroviral particles derived from SNV displaying targeting molecules other than antigen binding sites of an antibody are infectious, targeting envelopes were constructed that contained the receptor binding peptide of another virus (murine leukemia virus) fused to the envelope of SNV. Infectivity of virus particles displaying such targeting envelopes with and without wild-type envelope was tested.

EXAMPLES

Targeting Envelope

Materials and Methods Construction of Antibody-Envelope Fusion Genes

The gene coding for the envelope protein of spleen necrosis virus (SNV) does not contain suitable restriction enzyme sites to enable the construction of antibody-envelope fusion genes. Thus, point mutations were introduced (by site directed mutagenesis) in the SNV env gene at different locations to create restriction enzyme recognition sites. For this purpose, the SNV env gene (HindIII-SacI fragment) was subcloned into pSelect (a vector specifically designed for site directed mutagenesis). Restriction sites for enzymes that create blunt ends were introduced in such a way that the restriction enzymes cut between two codons. Following consistently this strategy, all mutants can be used to create deletions, insertions, and fusions in any combination without altering the reading frame. Further, restriction enzyme sites were nested between regions coding for hydrophobic and hydrophilic domains. It was hypothesized that the deletion of a certain domain(s) would not interfere with the proper folding of the following domain. This hypothesis is based on the finding that many proteins in evolution arose by exon shuffling of functional domains.

Some mutant envelopes that have been made are shown in FIG. 2. pSNV-env-mC (FIG. 2a) contains a new restriction enzyme site located between a hydrophobic and a hydrophilic peptide domain. In this mutant, the change in the nucleotide sequence does not alter the amino acid sequence. Thus, pSNV-env-mC can be considered as a positive control. pSNV-env-mD contains a new restriction enzyme site within the cleavage site of the envelope precursor. The introduction of the mutation also altered the amino acid sequence destroying the common motive found in all cleavage sites of all retroviruses investigated. Thus, it was expected that the resulting envelope precursor would not be cleaved, and, therefore, would not to give rise to infectious virus particles. Mutated env genes were inserted into pHB3, a eucaryotic gene expression vector (FIG. 2).

Figure 2A:
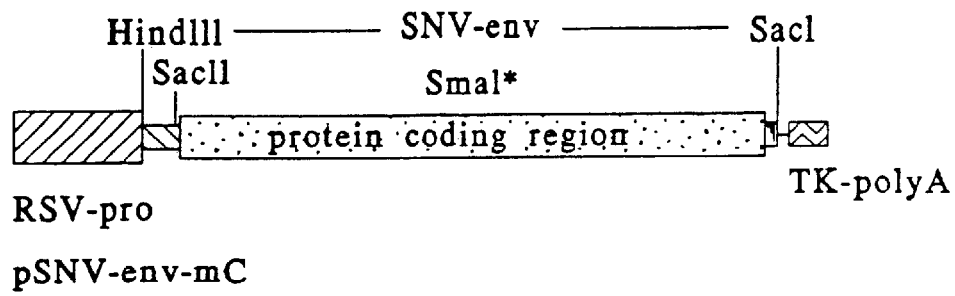
FIG. 2 (Parts A–E) is a diagram illustrating plasmids expressing mutant envelope genes of spleen necrosis virus (SNV).
Figure 2B:
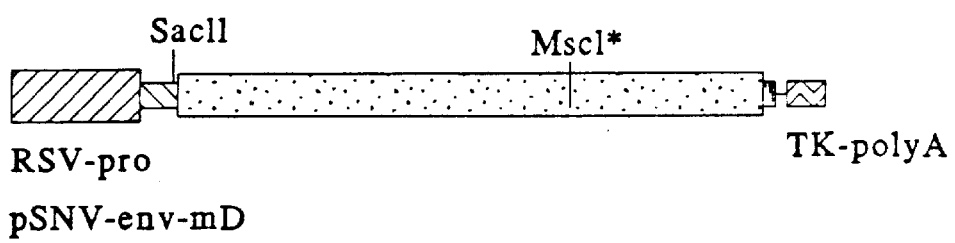
Figure 2C:
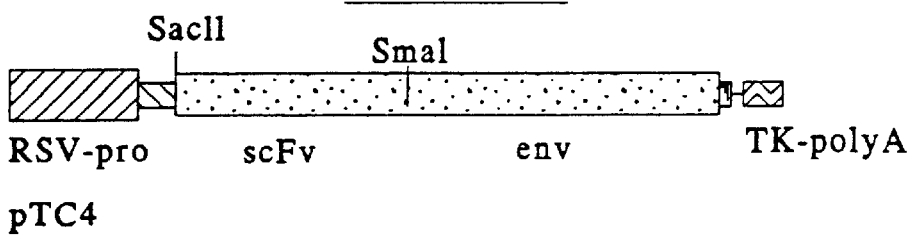
Figure 2D:
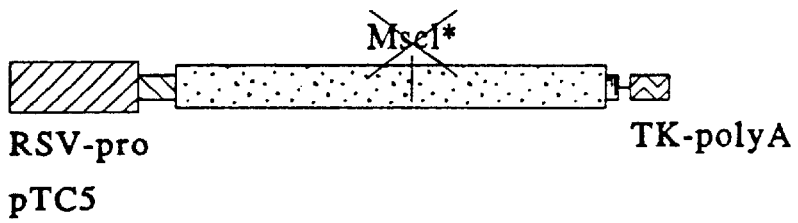
Figure 2E:
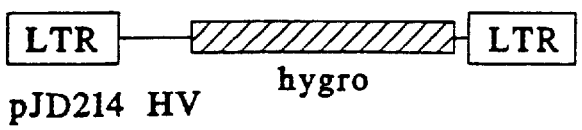

The genes coding for the heavy and the light chain of an antibody against DNP have been kindly provided by Dr. Ogawa (Scripps Clinic, La Jolla, Calif.). The genes were sequenced and published (Riley et al., 1986). Using PCR technology as described (Whitlow and Filpula, 1990), a single chain antibody gene was constructed including the signal peptide against DNP. The PCR product was cloned into the SmaI site of pBluescript. DNA sequencing confirmed the successful combination of the two gene segments coding for the variable regions of the antigen binding peptide. The complete sequence of the anti-DNP scFv gene is given in FIG. 3. A SacII (located in the polylinker of pBluescript) to SmaI (located in the 3' PCR primer) fragment was inserted into eucaryotic expression vectors replacing amino terminal parts of the envelope gene as follows: in PTC4, the SacII (located upstream of the ATG codon of the env gene) to SmaI fragment of env was replaced with the scFv gene' in pTC5 the SacII to the MscI fragment of env was replaced with the scFv gene (FIGS. 2C and 2D, respectively). After cloning, the antibody-envelope junctions were sequenced to verify the maintenance of the correct reading frame of the chimeric gene.

Binding Assays

The in vitro binding assays were performed in the following manner. DNP was conjugated to BSA (DNP-BSA was used to raise the initial antibodies from which the scFv genes have been derived). DNP-BSA was coupled to activated Sepharose following the protocol recommended by the supplier (Sigma). An Elisa assay with an anti-DNP antibody (kindly provided by Dr. S. Pestka) confirmed the successful coupling reaction. 100 ml of tissue culture supernatant medium was incubated with 50 ml of DNP-BSA-Sepharose for 30 minutes at 37° C. After incubation, the sepharose particles were pelleted by centrifugation in a Qualitron minicentrifuge for 30 seconds. The pellets were rinsed once with PBS. The PBS was removed and reverse transcription assays were performed by adding the reaction to the sepharose pellet. The reverse transcription assay was done using standard procedures; incorporation of 32PdTTP into cDNA was determined by TCA precipitation as described (Schleif and Wensink, 1981)

Test for Infectivity ff Particles Containing Antibody-Envelope Fusion Proteins

Figure 1A:
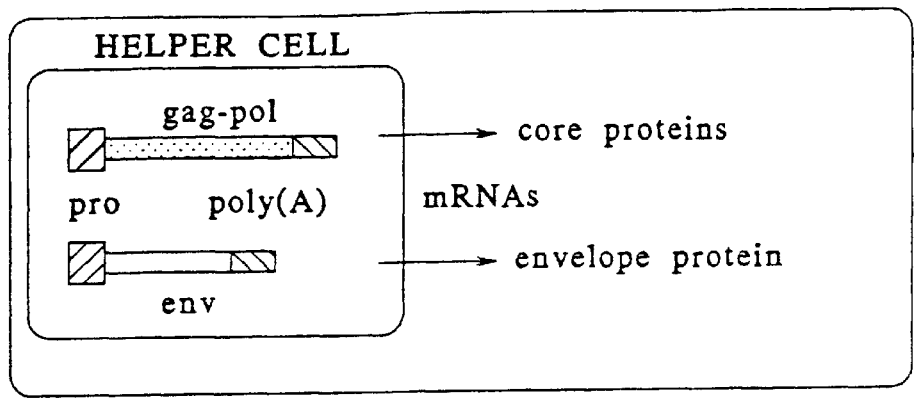
FIG. 1 (Parts A–C) is a diagram illustrating helper cells expressing retroviral proteins: (A) Helper cells are made by the transfection of plasmids expressing all retroviral proteins necessary to form infectious virus particles; (B) After transfection of the retroviral vector, the vector RNA genome is encapsidated into core structures: (C) Helper cells that contain a plasmid express a modified envelope gene.
Figure 1B:
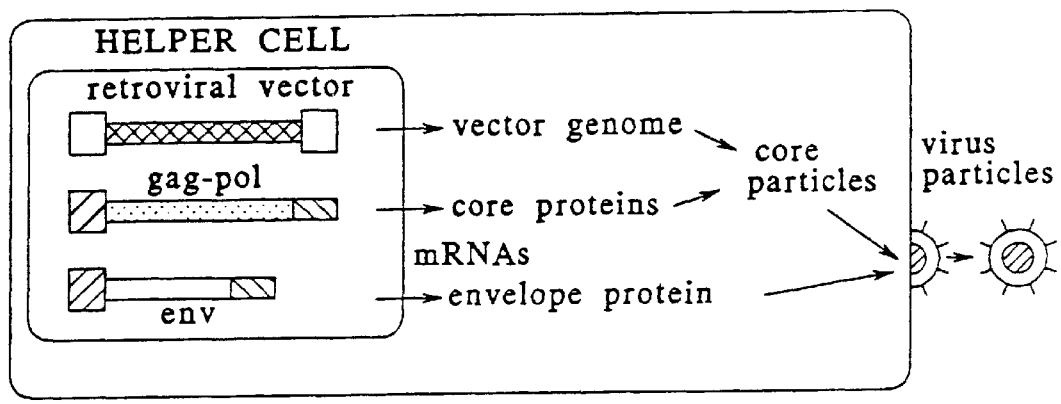
Figure 1C:
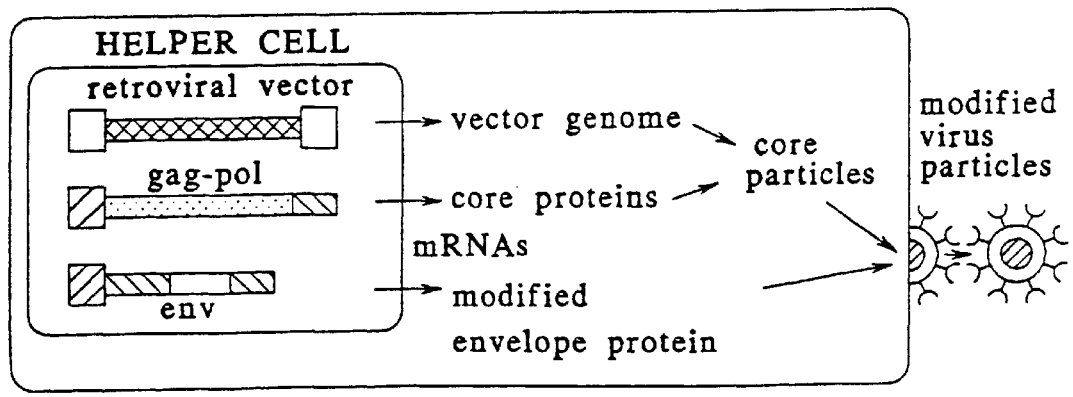

The envelope expression plasmids shown in FIG. 2 were transfected into D17 cells (a dog osteosarcoma cell-line) in contransfection with pBR1 and pJD214HY (FIG. 2), plasmids expressing the retroviral core proteins, and containing a retroviral vector for the expression of the hygromycin phosphotransferase gene, respectively (see also FIG. 1). Cells were selected for hygromycin resistance. After selection for hygromycin resistance, virus was harvested from confluent cell cultures and infectivity assays were performed (see below). Infected target cells were selected for hygromycin resistance (D17 cells were incubated with medium containing 60 mg/ml hygromycin, CHO cells with medium containing 250 mg/ml hygromycin). Hygromycin resistant cell colonies indicate infectious virus particles.

Infectivity assays were performed on D17 and CHO cells with and without conjugated DNP. DNP was conjugated to cells as follows: Cells were incubated with 500 ml of a solution containing 1.4 mg/ml DNBS (2,4,-Dinitrobenzenesulfonic acid, 2-hydrate, purchased from Kodak) in sodium cocodylate buffer (0.25M) for 3 to 5 minutes at room temperature. The conjugation reaction was stopped by adding 5 ml of medium to the cells.

Infections of non-conjugated cells were performed in the presence of 50 mM polybrene using standard protocols. In the case of DNP conjugated cells, infection was performed without polybrene.

Wild-Type Envelope

Material and Methods ScA Targeting Vectors

Figure 6:
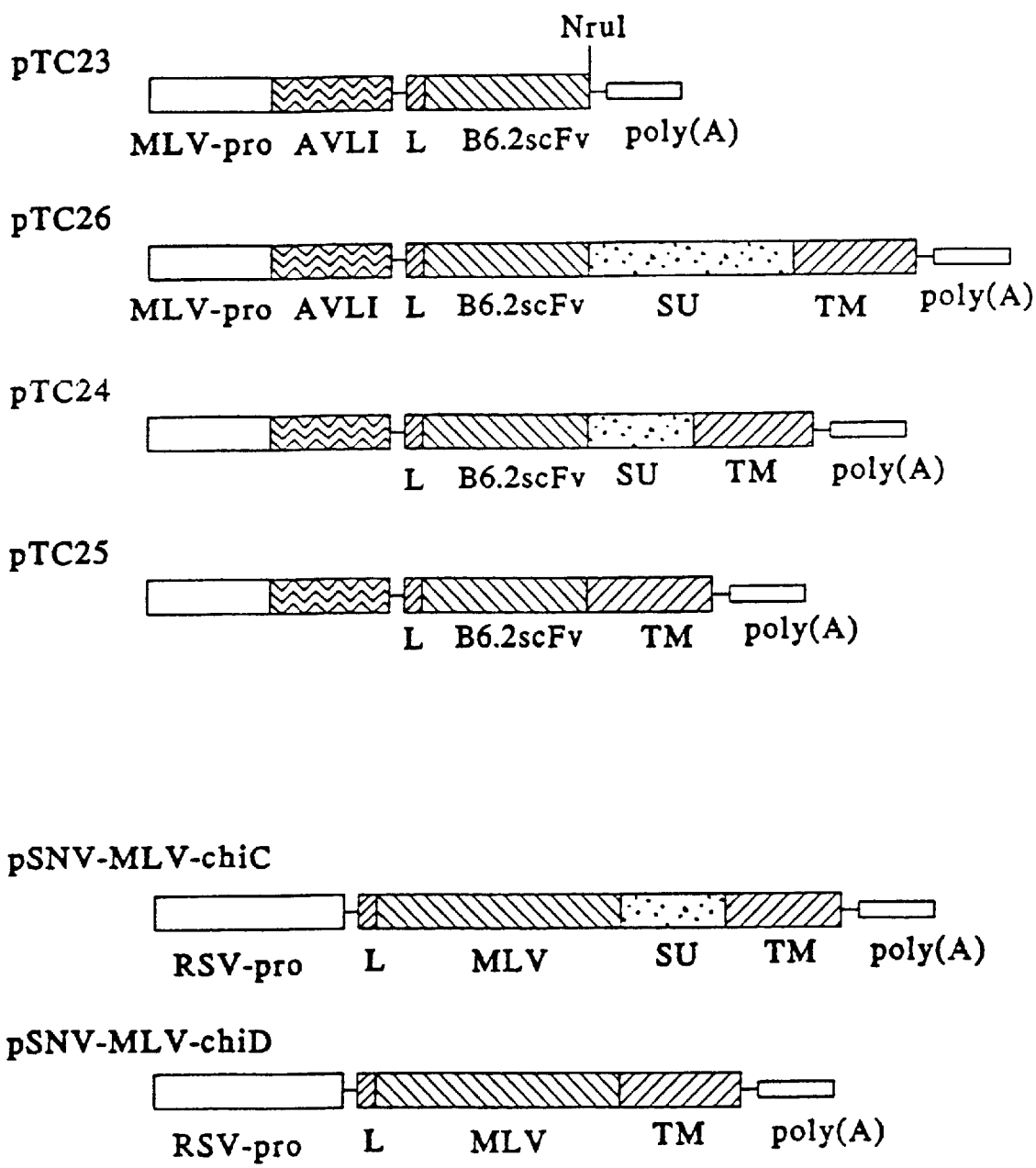
FIG. 6 is a diagram illustrating plasmids expressing spleen necrosis virus, SNV, core structure proteins, wild-type envelope proteins, and various targeting envelope proteins.

To construct a targeting envelope containing the antigen binding site of an antibody directed against a cell-surface protein expressed on several human tumor cells, the corresponding single chain antibody gene (termed B6.2, Bird, R. E. et al., 1988 and Colcher, D. et al., 1990) made for expression in *E.coli* was modified in the following way: PCR technology was used to amplify the B6.2 scA gene using the original *E.coli* expression plasmid as template (Bird, R. E. et al., 1988 and Colcher, D. et al., 1990). The primers used had the following sequence:
Primer A (SEQ ID NO:1): 5' GGAGCGCTGACGTCGT-GATGACCCAGTC 3'
Primer B (SEQ ID NO:2): 5' CCTCGCGATCCACCGCCG-GAGACTGTGAGAGTGGTGC 3'
The PCR amplification results in a fragment that does not contain the bacterial ompA signal sequence and the stop codons present in the original B6.2 gene (Bird, R. E. et al., 1988 and Colcher, D. et al., 1990). The PCR products were cloned into the SmaI site of the pBluescript vector (Strata gene) and sequenced to verify a correct reading frame. The plasmid was termed pTC9. The B6.2 gene was isolated by digesting the pTC9 plasmid with Eco47III plus NruI. The corresponding restriction enzyme recognition sites have been introduced with the primers used for PCR amplification. The B6.2 gene (the Eco47III to NruI fragment was cloned into pTC13, a gene expression vector (FIG. 5). The corresponding vector (termed pTC23) contains the ER transport signal sequence of the SNV envelope protein fused to the B6.2 gene to enable transport through the endoplasmatic reticulum. The cloning reconstituted the NruI site at the 3' end of the B6.2 gene. Carboxy terminal parts of the SNV envelope gene were isolated and fused to the B.2 gene (NruI site) to give plasmids pTC24, pTC25, and pTG26 (FIG. 6). These constructs are very similar to plasmids pTC4 and pTC5 which contain the anti-DNP antibody. In plasmid pTC26, the antibody is fused to codon 168 of the SNV envelope.

Chimeric SNV-MLV Targeting Envelope

Targeting envelopes containing the receptor binding peptide of another virus were made as follows: the gene segment of ecotropic murine leukemia virus (a HindIII-BalI fragment comprising almost the complete region coding for the SU peptide, including its ER transport signal sequence, Ott, D., and Rein, A. 1992) was isolated and inserted into the vectors pSNV-env-mC and pSNV-env-mD (pSNV-env-mC and pSNV-env-mD was described in FIG. 2) replacing the amino terminal parts of the SNV envelope gene. The resulting constructs are identical to plasmids pTC4 and pTC5, respectively, except that the anti-DNP antibody peptide (anti-DNP scA) is replaced by the receptor binding peptide of ecoMLV (FIG. 6, pSNV-MLV-chiC and pSNV-MLV-chi-D, respectively).

Experimental System

Briefly, helper cells were made as described above by transfecting plasmids expressing retroviral gag-pol proteins, the retroviral targeting envelope, and the wild-type envelope into D17 cells in co-transfection with a selectable marker to obtain helper cell lines containing targeting envelope only or helper cells containing both targeting and wild-type envelope. Infectivity assays were performed on a variety of different cell-lines which included D17 cells, CHTG-cells expressing the ecotropic murine leukemia virus receptor (Albritton, L. M. et al., 1989) and human HeLa and Col-1 cells. Infectivity was determined with a retroviral vector expressing the bacterial beta-galactosidase gene as described (Mikawa, T. et al.).

Results

Targeting Envelope

In vitro binding assay. The in vitro binding assays showed that only cells transfected with pSNV-env-mD produce viral vector particles that contain a chimeric envelope able to bind DNP (see also Table 1).

Infectivity studies. The results of the infectivity experiments are summarized in Table 1. Vector particles containing wild-type envelope (pSNV-env-mC) infected D17 cells with an efficiency of about $10^5$ (=100,000) colony forming units per ml of tissue culture supernatant medium. Such virus particles also infected D17 cells conjugated with DNP. However, the efficiency of infection was three orders of magnitude less than that of cells not conjugated with DNP. This drop in virus titer is mainly due to difficulties of selecting DNP conjugated cells with the antibiotic. It appears that the conjugation reaction makes cells very vulnerable to the drug and more than 90% of the cells died two to three days after the conjugation action. Virus particles with wild-type envelope do not infect CHO cells.

The mutation of the cleavage site of the envelope precursor protein (SNV-env-mD) completely abolished infectivity.

Only one colony was observed in D17 cells not conjugated with DNP. This finding coincides with earlier reports that mutations in the envelope precursor cleavage site lead to non-infectious virus particles. Cells transfected with pTC4 (FIG. 2) did not produce vector particles that were able to infect D17 or CHO cells at significant efficiencies. Cells transfected with pTC5 produced virus particles unable to infect D17 or CHO cells. However, such particles significantly infected cells conjugated with DNP.

Wild-Type Envelope

First, the presence of wild-type envelope in particles displaying an antigen binding site against DNP was tested to determine whether there would be an increase in the efficiency of infection of cells conjugated with DNP. It was found that DNP conjugated HeLa cells could not be infected with vector virus particles that contained the wild type envelope alone. However, DNP conjugated cells could be infected with anti-DNP displaying retroviral vectors at a very low efficiency. The titer measured was about 10 infectious units per ml of tissue culture supernatant medium. Virus particles that contained wild-type envelope in addition to the targeting anti-DNP envelope infected cells 10 to 30 times more efficiently. This data indicate that the presence of wild-type envelope can increase the efficiency of infection of targeting vectors. Two additional sets of experiments using other targeting molecules were performed to corroborate this finding.

1. Infectivity studies with virus particles containing antibody-envelope fusion proteins. D17 cells, HeLa cells and Col-1 cells were infected with virus particles displaying an antigen binding site of an antibody (B6.2, Bird, R. E. et al., 1988 and Colcher, D. et al., 1990) directed against a cell surface protein expressed on various human carcinoma cells. Vector virus particles were harvested from a variety of different helper cell lines (Table 2). All virus particles were carrying a vector transducing the bacterial beta-galactosidase gene. Infectivity was determined by staining the cells with X-gal as described (Mikawa, T. et al.). The number of blue cell colonies was determined two to three days after infection. The following virus particles were tested for infectivity: virus particles that do not contain envelope (termed "no env"), virus particles that contain wild-type envelope alone (termed wt-env—DSN), virus particles that contain targeting envelopes alone which are antibody-envelope fusion proteins (termed TC24, TC25, and TC26 as described in FIG. 6), and particles that contain wild-type plus targeting envelopes (termed TC24+wt-env, TC25+wt-env, and TC26+wt-env).

Particles that do not contain any envelope were found to be basically not infectious. Particles that contain wild-type envelope were infectious only on D17 cells which contain a viable receptor for wild-type SNV. The particles were not infectious on HeLa cells or Col-1 cells. Particles that contained targeting envelopes only were infectious on D17 and HeLa cells. The efficiency of infection on D17 cells was less than 5% of that of virus containing wild-type envelope. Such particles were not infectious on Col-1 cells. The addition of wild-type envelope increased efficiency of infection 10 to 50 fold. Further, Col-1 cells that could not be infected with particles containing either envelope alone could be infected with particles containing both wild-type env and targeting env. This data indicates that the wild-type envelope adds a function improving or even completely enabling virus penetration (Table 2). These data also show that the level of infectivity is dependent on the position within the envelope gene at which the antibody is fused to the envelope.

2. Infectivity studies with virus particles containing SNV-MLV-fusion proteins. CHTG cells (described in Albritton, L. M. et al., 1989) expressing the receptor of ecotropic murine leukemia virus as well as D17 cells were infected with virus harvested from cells expressing targeting envelopes (SNV-MLV-chi-C and SNVMLV-chic-D) alone or from helper cells expressing targeting envelope plus wild-type envelope. Virus particles were carrying to hygromycin B resistance gene. Infected cells were selected from hygromycin resistance and the number of hygromycin resistant cell colonies was determined. Retroviral vector particles containing the targeting envelope alone were not infectious. The particles became infectious after wild-type envelope was added to the particles. Particles with wild-type envelope alone are not infectious on CHTG cells (Table 3).

Discussion

Targeting Envelope

The data obtained with retroviral particles containing antibody-envelope fusion proteins showed that such particles are competent for infection. Surprisingly, TC4, a construct that contains the scFv gene fused to env in the middle of SU did not give virus particles capable of binding DNP. This may be due to an unstable SU-TM complex. This hypothesis is supported by the finding that such particles failed to bind to DNP-BSA-Sepharose. Low level infectivity of such particles on D17 cells may result from unspecific adsorption of virus particles containing TM only. Unspecifically adsorbed virus particles (depleted of SU) may occasional penetrate the cell.

Cells transfected with pTC5 produce virus particles with chimeric envelopes without a functional retroviral membrane fusion domain. This assumption is based on the finding that virus particles containing uncleaved envelope precursor proteins (SNV-env-mD) are not infectious. However, it is known that some antibody molecules are internalized by cells after binding to cell surface by an unknown mechanism. The data show that such an internalization mechanism might be sufficient to allow internalization of the virus particle and the consequent establishment of a successful infection.

Applications of Vector Particles with Antibody-Envelope Fusion Proteins in Gene Therapy In all applications of human gene therapy so far, the cells of interest were isolated from the patient, purified from other cell types, and infected in tissue culture with retroviral vector particles which were harvested from helper cells. After expansion of the treated cells in tissue culture, they were re-injected into the patient. The infection of cells has to be done in vitro, since the retroviral vector particles used (derived from amphotropic murine retroviruses) have a broad host range. Thus, if injected directly into the blood stream of a patient, such virus particles would infect all kinds of tissue. Besides other risks, this treatment would be inefficient, since the chance that the gene will be delivered to its appropriate target cell is very low.

This clinical gene therapy protocol may be sufficient to obtain insight into how efficient and how beneficiary gene therapy will be for the patient. Indeed, the clinical data look very promising (Eglitis, personal communication). However, the current clinical protocol is very laborious, time consuming, very costly, and, therefore, not suitable for general clinical application. For general clinical application, it will be necessary to inject the gene transfer vehicle directly into the body of the patient.

The development of a retroviral vector particle that only infects one specific cell type, may allow the direct injection of the vector into the patient's blood stream. The development of vector particles containing antibody-envelope chimeras may be the first step towards this goal and may open a new area of possible applications of gene therapy in vivo.

In Vivo Delivery of Therapeutic Genes with Retroviral Vectors that Display Single Chain Antibodies To test in vivo gene delivery wit h retroviral vector particles that display single chain antibodies on the viral surface, SCID mice have been used as a first model system. It is well known that retroviral vectors are rapidly inactivated by complement, if they are produced from cells of a heterologous species. However, SCID mice do not have a functional immune system.

Confirmation that SCID mouse serum does not inactivate SNV retroviral particles. In our experiments, retroviral vector particles were harvested from DSH-cxl packaging lines (described in Martinez and Dornburg, Virology, 208: 234–241, 1995; Chu an d Dornburg, J. Virol. 69: 2659–2663, 1995). These packaging cells transduce a retroviral vector expressing the bacterial β-galactosidase gene (lacZ gene). The plasmid pCXL (Mikawa T. D., et al., Exp. Cell Res., 195: 516–523, 1992) contains a SNV-derived retroviral vector expressing the lacz gene. Aliquots of 100 μl of the retroviral vector solution were prepared and incubated with 0.1, 1, 10, and 100 μl of SCID mouse serum for 10 minutes, respectively. In a second experiment, the same amounts of heat-inactivated (60° C. for 30 minutes) SCID mouse serum were added to 100 μl of vector stocks. Next, the mixtures were added to $2 \times 10^5$ D17 cells in infectivity assays. Two days after this infection the cells were stained with x-gal and the number of blue colonies was determined as described (Martinez and Dornburg, Virology, 208: 234–241, 1995; Chu and Dornburg, J. Virol 69: 2659–2663, 1995). No significant differences in infectivity were observed between samples incubated with fresh or heat-inactivated serum. Thus, the conclusion can be made that SCID mouse serum does not contain antibodies and/or complement factors which inactivate SNV retroviral particles.

Cell type specific gene delivery in vivo. In another experiment, hygromycin-resistant human COLO320DM cells, which express the cell surface marker Her2neu, (ATCC accession No. CCL 220) or hygromycin-resistant A431 cells, which do not express Her2neu (ATCC accession No. HB-9629), were injected into the peritoneum of mice. The next day, vector virus particles, which displayed anti-Her2neu single chain antibodies ($10^6$ infectious particles) were injected. The preparation of these virus particles is described below. The vector virus particles transduced a marker gene, the bacterial beta-galactosidase gene, into infected cells. Thus, by staining cells after infection, gene transduced cells stain blue and, therefore, can be easily detected.

Construction of packaging cell lines. The construction of stable packaging cells, which produce retroviral vector particles displaying the anti-Her2neu antibody followed the protocol described in detail in Chu, T.-H. and Dornburg, R., J. Virol 71: 720–725, 1997. Briefly, using the dog D17 cell-derived cell line DSgp13-cxl which expresses the encapsidation-negative SNV gag-pol proteins and the packagable retroviral vector pCXL, cell lines were made which expressed the chimeric scA-env fusion proteins. For this, the scA-Env gene expression vector pAJ7 (described below) was transfected into DSgp13-xcl cells in co-transfection with a plasmid expressing a selectable marker gene. In this experiment, we used the puromycin resistance gene, driven by the SNV promoter, contained on pRD118-puro, derived from pRD118 (Chu, T. H. et al., Bioteching, 18: 890–899, 1995) . However, one skilled in the art would be able to readily to select an appropriate selectable marker gene. About 100 to 200 single antibiotic resistant cell colonies were isolated for each transfection. Expression of the scA-Env protein was tested by ELISA assays and infectivity assays as soon as cells had been transferred to 24 well plates. The reason for making helper cells this way is that transfected plasmid DNAs often integrate into rather inactive chromosomal sites are poorly transcribed.

Figure 7:
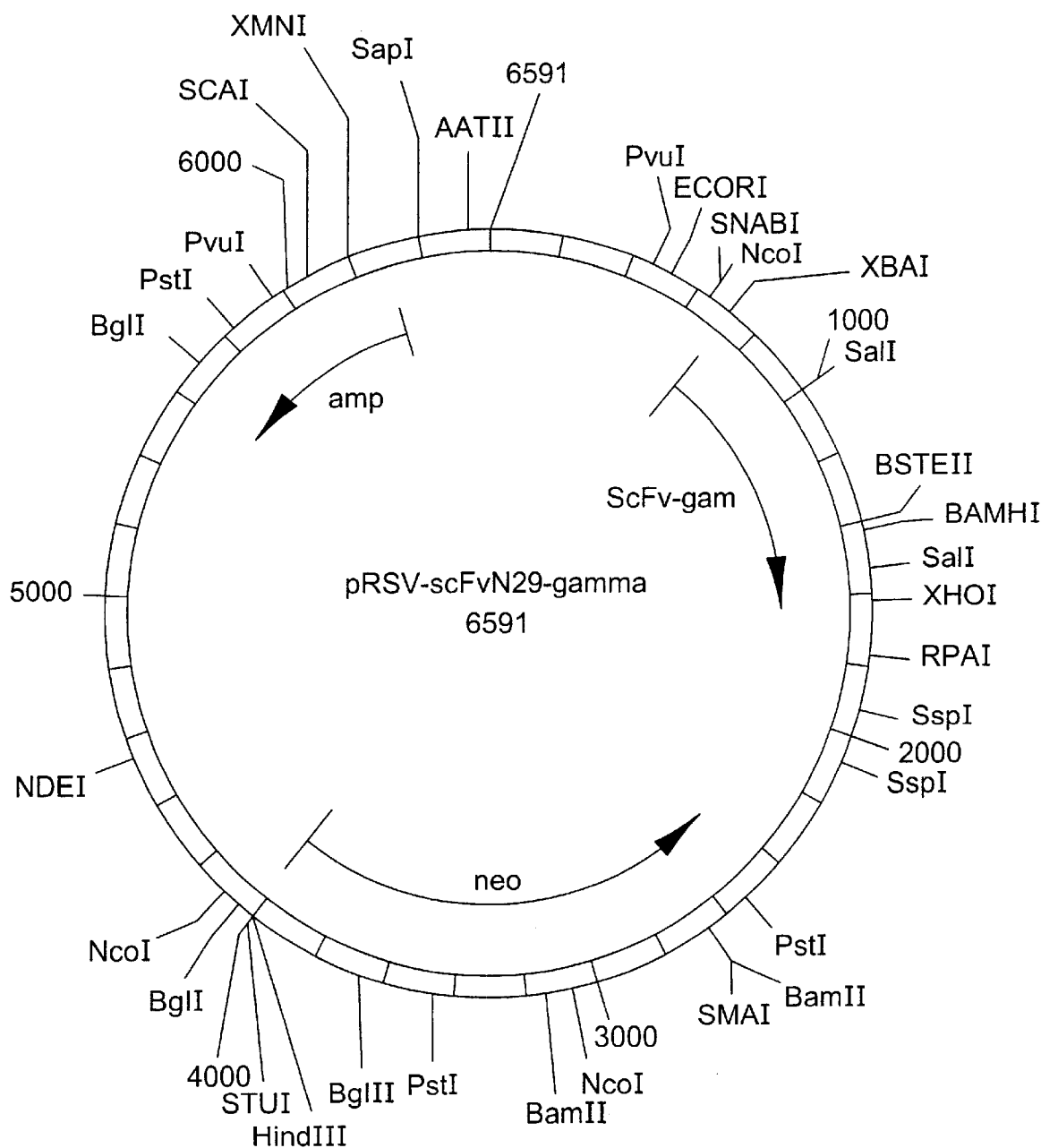
FIG. 7 is a restriction map of pRSV-scFvN29-gamma expressing the anti-Her2neu single chain antibody gene including the authentic hydrophobic leader sequence.
Figure 9:
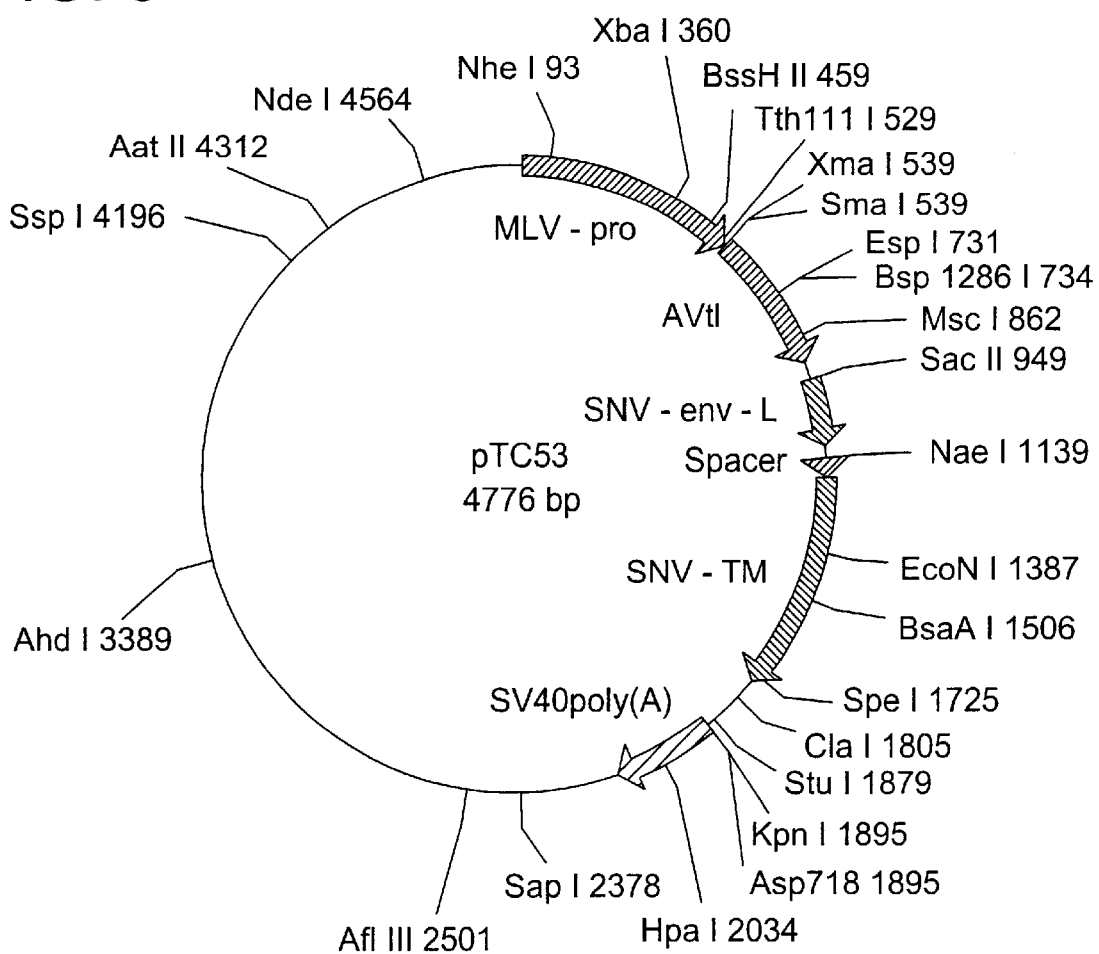
FIG. 9 is a restriction map of pTC53. PCR products of single chain antibody genes can be cloned into the NaeI site and the resulting construct expresses a chimeric envelope, which is transported through the ER and displayed on the surface of SNV derived retroviral vector particles.

Next, the SNV wild-type envelope gene expression vector pIM29 (Martinez, I. and Dornburg, R., J. Virol. 69:4339–4346, 1995; and Martinez, I. and Dornburg, R. Virology 208:234–241, 1995) was transfected into cell lines established from the single colonies described above. Again, the transfection was done by co-transfecting a plasmid expressing a selectable marker (e.g., the hygromycin B phosphotransferase gene). 100 to 200 single cell colonies were isolated and tested for infectivity on human target cells. Cell clones with the highest infectivity were selected, re-cloned once or twice, and finally used for in vivo experiments.

pAJ7 is a plasmid containing the anti-Her1neu scA fused to the SNV-Env-TM coding region. This plasmid is very similar to plasmid pTC25 (FIG. 6). However, it was made in a slightly different way: First, referring to FIGS. 7 and 8, a DNA linker coding for the amino acids ala-gly-ala-ser-gly-ser was inserted at the carboxy terminal end of the anti-Her2neu scA gene (which contains the authentic hydrophobic leader sequence of the antibody-gene for transport through the ER) in plasmid N29-gamma to give plasmid pRD161 (not shown). A DNA fragment (SnaB1 to Eco47III) isolated from pRD161 and which contained the complete anti-Her2neu scA (including the hydrophobic leader sequence) were cloned into pTC53 (FIG. 9) digested with Sac2 (blunt ended) plus NaeI to give plasmid pAJ7. DNA sequencing was performed after all cloning steps to verify the maintenance of the correct reading frame of genes coding for the chimeric protein.

Plasmid pTC53 (FIG. 9) is a gene expression plasmid for the fast cloning and efficient expression of single chain antibody-envelope fusion proteins for display on retroviral particles. pTC53 has been derived from pTC13 (Chu, T.-H. and R. Dornburg, 1995, J. Virol. 69: 2659–2663; and Chu, T.-H., et al., 1995, Biotechniq. 18: 890–899). It contains the MLV-U3 promoter and the Adenovirus 2 tripartite leader sequence followed by a sequence coding for the hydrophobic leader sequence of the SNV envelope gene Next, the plasmid contains a unique NaeI site (which cuts between two codons) for cloning of single chain antibody genes (e.g. PCR products). Downstream of the NaeI site is a DNA linker coding for the amino acid motif $(gly_4\text{-}ser)_3$ to enable flexibility of the scA. This gly-ser linker is fused in frame to the complete transmembrane peptide (TM) coding region of the SNV envelope gene. The polyadenylation site downstream of the TM coding region has been derived from simian virus 40 (SV40). The plasmid backbone is that of pUC19.

Concentration of vector virus stocks. Concentrated vector virus stocks were prepared as described by Chu and Dornburg, J. Virol. 71:720–725, 1997. Briefly, to concentrate the virus particles by ultrafiltration, 15 ml of supernatant was added to Amicon Centriprep filtration devices containing 100, or 500 kD molecular weight cut-off (MWCO) membranes (Amicon, Beverly, Mass.). The 100 kD cut-off membranes are made of cellulose, the 500 kD membrane is made of polysulfone (David Brewster, Amicon, personal communication). The vector particle solution was centrifugated in a Sorvall RC5000B table top centrifuge with swing-out buckets at 3,000 rpm for 30 min at 20° C. The supernatant medium was discarded and the solution was centrifugated at least one more time for 10 minutes or until a final volume of 1 ml (or less, e.g., 0.7 ml) was obtained. The final concentrate was used immediately for the infectivity experiments.

Confirmation of cell-type specific gene delivery in-vivo. The day after vector virus injection, the mice were sacrificed. Human cells were recovered by trypsin treatment of the peritoneum. The cells were isolated and subjected to different antibiotic selection in tissue culture. Hygromycin selection enables the growth of human COLO320DM Her2neu+target cells or A431 Her2neu- non-target cells but not the mouse cells. In both experiments, human cells started to grow as colonies in a vast background of mouse cells. 4 days after selection, the cells were stained with x-gal. (Chu, T.-H. and R. Dornburg. 1997. J. Virol 71: 720–725). We found that 2 to 3% of the COLO320DM target cells were infected in vivo. None of the A431 were infected. Furthermore, none of the mouse cells (mainly epithelial cells of the peritoneum) stained blue indicating that they were not infected. This data indicates that a cell-type specific gene delivery can be obtained in vivo and that SCID mice are suitable model systems to study in vivo gene delivery.

Wild-Type Envelope

Retroviral vector particles which display an antigen binding site of an antibody can specifically infect cells that contain an antigen specific for the antibody. However, the efficiency of the gene transfer can be low. We hypothesized that the fusion of the targeting peptide to the envelope impaired the natural fusion function of the envelope which is essential for efficient penetration of the virus. Thus, the hypothesis that the addition of a wild-type envelope may complement this shortcoming was tested.

New retroviral vector particles containing two different types of targeting envelopes were constructed. These targeting envelopes were (1) fusion proteins containing the antigen binding site of an antibody fused to various carboxy terminal portions of the envelope protein of spleen necrosis virus, SNV; and (2) fusion proteins consisting of the receptor binding domain of ecoMLV fused to various carboxy terminal portions of the SNV, similar to the antibody envelope constructs (FIG. 6).

Targeting envelopes alone are little or not infectious on cells that contain a receptor for the targeting envelope. The addition of wild-type envelope to particles containing targeting envelopes dramatically increased or even completely enable infectivity on target cells that could hardly or not at all infected with virus particles containing either envelope alone. This data show that the construction of particles containing mixed envelopes dramatically improves the efficiency of gene transfer into specific target cells and, therefore, provides a valuable tool to introduce genes into specific target cells.

This method can be probably be improved by mutating the natural receptor binding domain of the wild-type envelope (e.g., by site directed mutagenesis). Using a wild-type envelope containing a non-functional receptor binding site in mixed envelope retroviral vector particles may enable to also target cells that contain a receptor for the wild-type envelope without loosing target cell specificity.

TABLE 1

Infectivity of Retroviral Vector Particles On D17 and CHO Cells With and Without DNP Conjugation*

| Envelope of virus particle | Binding to DNP | Virus titer (cfu/ml) D17 cells | Virus titer (cfu/ml) D17 + DNP | CHO − DNP | CHO + DNP |
|---|---|---|---|---|---|
| SNV-env-mC | nd | $10^5$ | $10^2$ | 0 | 0 |
| SNV-env-mD | — | 1 | 0 | 0 | 0 |
| TC4 | — | 10 | 0 | 0 | 1 |
| TC5 | + | 0 | $10^2$ | 0 | 10 |

*Virus was harvested from tissue culture cells expressing SNV gag-pol and the envelope protein indicated n the left column (see also FIG. 2). All cells contained pJD214HY, a retroviral vector expressing the hygromycin B phosphotransferase gene. Infected cells were selected for hygromycin resistance. The number of hygromycin resistant cell colonies was determined two to three weeks after infection (after all cells had died in uninfected control plates). DNP binding of vector particles was the determined by measuring reverse transcriptase activity bound to DNP-BSA-Sepharose particles. nd: not determined; 0: no hygromycin resistant colonies were detected. Virus titers are expressed as colony forming units (cfu) per ml of tissue culture supernatant medium.

TABLE 2

Infectivity of Retroviral Vector particles Displaying the B6.2 Single Chain Antigen Binding Peptide

| Construct gag-pol + | Titer (CFU/ml) D17 | HeLa | COL-1 |
|---|---|---|---|
| no env | 1 | nd | -* |
| wt-env (dsn) | 1,000 | nd | nd |
| TC26 | 40 | 10 | nd |
| TC24 | 20 | 5 | nd |
| TC25 | 45 | 20 | nd |
| TC26 + wt-env | 1,100 | 90 | 45 |
| TC24 + wt-env | 10,000 | 250 | 115 |
| TC25 + wt-env | 4,000 | 100 | 55 |

-* experiment not done.
nd: no infected cells were detected in infection experiments using a total of 2 ml supernatant tissue culture medium.

TABLE 3

Infectivity of Retroviral Vector Particles Containing Chimeric Envelope Proteins of MLV and SNV

| Envelope of virus particle cells | Virus titer (cfu/ml) D17 cells | CHTG |
|---|---|---|
| MLY-SNV-chiC | nd | nd |
| MLV-SNV-chiD | nd | nd |
| MLV-SNV-chiC + wt SNV | $10^6$ | $10^3$ |
| MLV-SNV-chiD + wt SNV | $10^6$ | $10^3$ |
| DSN | $10^5$ | nd |

Virus was harvested from tissue culture cells expressing SNV gag-pol and the envelope protein indicated in the left column (see also FIG. 6). All experiments were performed with pJD214HY a retroviral vector transferring the hygromycin resistance gene. Virus titers are expressed as hygromycin resistant colony forming units per ml of tissue culture supernatant medium. SNV-MLV-chiC+wt SNV and SNV-MLV-chiD+wt SNV are cell lines expressing chimeric envelopes of MLV and SNV plus the envelope of wild type (wt) SNV. DSN cells are SNV based helper cells expressing gag-pol and SNV env from two different plasmid constructs. Virus titers are expressed as colony forming units (cfu) per ml of tissue culture supernatant medium. Nd: no hygromycin resistant colonies were detected using a total of 5 ml tissue culture medium.

The term "oligonucleotide" as used herein refers to primers, probes, oligomer fragments to be detected, oligomer controls, and unlabeled blocking oligomers. Oligonucleotide are molecules comprised of two or more deoxyribonucleotides or ribonucleotides. The term "primer" as used herein refers to an oligonucleotide, preferably an oligodeoxyribonucleotide, either naturally occurring such as a purified restriction digest or synthetically produced, which is capable of acting as a point of initiation of synthesis when subjected to conditions in which synthesis of a primer extension product, which is complementary to a nucleic acid strand, is induced, i.e., in the presence of nucleotides, an agent for polymerization such as a DNA polymerase, and a suitable temperature and pH. The primer must be sufficiently long to prime the synthesis of extension products in the presence of the polymerization agent. Methods for amplifying and detecting nucleic acid sequences by polymerase chain reaction (PCR) are described in detail in U.S. Pat. Nos. 4,683,195, 4,683,202, and 4,965,288, which disclosures are incorporated herein by reference.

FIG. 1 is a diagram illustrating helper cells expressing retroviral proteins. A) Helper cells are made by the transfection of plasmids expressing all retroviral proteins necessary to form infectious virus particles. One plasmid is designed to express all core/proteins (expression of gag and pol). The other plasmid is designed to express the envelope precursor/protein. Both plasmid constructs do not contain retroviral cis/acting sequences for virus replication (e.g., encapsidation sequences, a primer building site etc.). Polyadenylation takes place in non/retroviral polyadenylation recognition sequences. B) After transfection of the retroviral vector, the vector RNA genome is encapsidated into core structures. The helper cell is producing retroviral particles that only contain the vector genome with the gene(s) of interest. The vector contains all cis/acting sequences for replication. Thus, in infected target cells, the vector genome is reverse transcribed and integrated into the genome. Due to the lack of retroviral protein coding genes in the vector genome, no virus particles are produced from infected target cells. C) Helper cells that contain a plasmid express a modified envelope gene. The helper cell is very similar to that shown above. However, chimeric envelope genes were constructed that contain the antigen binding domain of an antibody at the amino terminus fused to the carboxy terminus of the envelope gene. Such particles may only bind to and infect target cells that contain an antigen structure which is recognized by the antibody moiety of the chimeric envelope protein.

FIG. 2 is a diagram illustrating plasmids expressing mutant envelope genes of spleen necrosis virus (SNV). Genes are expressed from the Rous sarcoma virus promoter (RSV/pro) and polyadenylated within the polyadenylation signal of herpes simplex virus thymidine kinase gene (TK/poly(A)). The polylinker of pBluescript was inserted between the promoter and the polyadenylation sequence to allow the easy cloning of genes into this vector (plasmid sequences that abut the vector are not shown). a/b) point mutations were introduced into the env gene by site directed mutagenesis to create new restriction enzyme recognition sites (indicated by an *). All enzymes cut exactly between two codons creating blunt ends for easy ligation without shifting the reading frame. c/d) chimeric envelope of containing an antigen binding peptide fused to the carboxy terminus of env. e) pJD214Hy, a retroviral vector used in all studies to test the transfer of genes by retroviral vector particles.

FIG. 3 shows the sequence of the single chain antibody gene (scFv) against the hapten DNP.

FIG. 4 illustrates retroviral packaging cells. A) A eucaryotic cell containing two different plasmids for the production of retroviral vector particle proteins. A retroviral vector transfected into such cells and carrying the gene of interest is encapsidated by retroviral core proteins. The envelope expression vectors expresses targeting envelopes (e.g., an antigen binding peptide fused to the envelope). Virus particles are produced that infect a target cell only that contains a receptor specific for the antigen binding site. The helper shown under B) is similar to that shown above except that it also contains a gene expression vector coding for the wild-type envelope. Virus particles produced from such helper cells contain "mixed" envelopes which consist of the targeting envelope and the wild-type envelope. Formation of mixed oligomers is possible because both, the targeting as well as the wild-type envelope contain a complete TM peptide which mediates the formation of oligomers.

FIG. 5 illustrates a eucaryotic gene expression vector (pTC13) to obtain high level of gene products that contain an ER recognition sequence. The vector shown has been derived from another gene expression vector (termed pRD114) which is described in Sheay, W. et al., 1993. The vector shown differs from pRD114 in that it contains a gene fragment coding for an ER recognition signal sequence to enable the transport of proteins through the endoplasmatic reticulum. It contains two recognition sites for the restriction enzymes NruI and StuI which cut between two codons downstream of the ER signal sequence coding region. DNA fragments coding for any peptide can be inserted into this vector. Translation of the inserted gene is terminated by using one of the three stop codons. MLV-U3-pro: promoter and enhancer of murine leukemia virus; Ad. V. leader: tripartite leader sequence of adenovirus; SV40 poly(A): polyadenylation signal sequence of simian virus 40.

FIG. 6 illustrates plasmid vectors expressing targeting envelope proteins. The PCR product of the gene coding for the single chain antibody B6.2 (a Eco47III to NruI fragment, see Material and Methods) was cloned into the NruI site of pTC13 (FIG. 5) to give plasmid pTC23. Carboxy terminal parts of the SNV envelope gene were isolated and cloned into the NruI site downstream of the B6.2 antibody gene. The resulting targeting antibody-envelope fusion gene of pTC24 and pTC25 are similar to pTC4 and pTC5. pTC24 and pTC25 retain exactly the same amount of SNV envelope as pTC4 and pTC5, respectively. In pTC26 the antibody coding genes abuts the envelope coding region at codon 167 of the envelope gene. Plasmids pSNV-MLV-chiC and pSNV-MLV-chiD are identical to pTC4 and pTC5, except that the antibody gene is replaced with a gene fragment encoding for almost the complete SU peptide of MLV. In these clones the ER transport signal sequence (L) is from MLV. MLV-pro: promoter and enhancer of murine leukemia virus; Avtl: tripartite leader sequence of adenovirus; L: ER transport signal sequence, B6.2scFV: gene encoding the single chain antibody B6.2; poly(A) polyadeylation signal sequence of SV40; SU surface peptide coding region of the SNV envelope; TM: transmembrane coding region of the SNV envelope; RSV: promoter and enhancer of Rous sarcoma virus.

APPENDIUM OF REFERENCES

Albritton, L. M., Tseng, L., Scadden, D., and Cunningham, J. M. 1989. A putative murine ecotropic retrovirus receptor gene encodes a multiple membrane-spanning protein and confers susceptibility to virus infection. Cell 57:659–666.

Battini, J. L., Heard, J. M. and Danos, O. (1992) Receptor choice in the envelope glycoproteins of amphotropic, xenotropic, and polytropic murine leukemia viruses. J. Virol. 66:1468–1475.

Bird, R. E., Hardman, K. D., Jacobson, J. W., Johnson, S., Kaufman, B. M., Lee, S. M., Lee. T., Pope, S. H., Riordan, G. S., and Whitlow, M. 1988. Single-chain antigen binding proteins. Science, 242; 423–426.

Chu, T.-H. and R. Dornburg. 1995. Retroviral vector particles displaying the antigen-binding site of an antibody enable cell-type-specific gene transfer. J. Virol. 69: 2659–2663.

Chu, T.-H. and R. Dornburg. 1997. Towards highly-efficient cell-type-specific gene transfer with retroviral vectors that display a single chain antibody. J. Virol. 71: 720–725.

Chu, T.-H., I. Martinez, P. Olson, and R. Dornburg. 1995. Highly efficient eucaryotic gene expression vectors for peptide secretion. Biotechniq. 18: 890–899.

Colcher, D., Bird., R., Roselli, M., Hardman, K. D., Johnson, S., Pope, S., Dodd, S. W., Pantoliano, M. W., Milenic, D. E., Schlom, J. 1990. In vitro tumor targeting of a recombinant single chain antigen-binding protein. J. Natl. Canc. Inst. 82: 1191–1197.

Cone, R. D. and Mulligan, R. C. 1984. High-efficiency gene transfer into mammalian cells: generation of helper-free recombinant retrovirus with broad mammalian host range. Proc. Natl. Acad. Sci. USA 81: 6349–6353.

Cournoyer, D., Scarpa, M., Jones, S. N., Moore, K. A., Belmont, J. W., and Caskey, C. T. 1990. Gene therapy: a new approach for the treatment of genetic disorders. Clin. Pharmacol. Ther. 47(1): 1–11.

Danos, O. and Mulligan, R. G. 1988. Safe and efficient generation of recombinant retroviruses with amphotropic and ecotropic host ranges Proc. Natl. Acad. Sci. 85: 6460–6464.

Davis, M. M. and Metzger, H. 1983. Structural basis of antibody function. Annu. Rev. Immunol. 1:87 117.

Dougherty, J. P. and Temin, H. M. 1989. New retrovirus helper cells with almost no nucleotide sequence homology to retrovirus vectors. J. Virol. 63, 3209–3212.

Friedman, T. 1989. Progress toward human gene therapy. Science 244, 1275–1281.

Gritz, L., and J. Davies 1983. Plasmid encoded hygromycin B resistance: the sequence of hygromycin B phosphotransferase gene and its expression in *Escherichia coli* and *Saccharomyces cerevisiae*. Gene 25, 179–188.

Hunter, E. and Swanstrom R. 1990. Retrovirus envelope glycoproteins. Curr. Top. Microbiol. Immunol. 157:187–253.

Kohn, D. B., Anderson, W. F., and Blaese, M. B., 1989. Gene therapy for genetic diseases. Cancer Investigation 7(2):179–192.

Larson, S. M. 1990. Improved tumor targeting with radiolabeled, recombinant, single-chain, antigen-binding protein. J. Natl. Canc. Inst. 82: 1189–1190.

Markowitz, D., Goff, S., and Bank, A. 1988. A safe packaging line for gene transfer: separation of viral genes on two different plasmids. J. Virol. 62:1120–1124.

Martinez, I. and R. Dornburg. 1995. Mapping of receptor binding domains in the envelope protein of spleen necrosis virus. J. Virol. 69: 4339–4346.

Martinez, I. and R. Dornburg. 1995. Improved retroviral packaging lines derived from spleen necrosis virus. Virology 208: 234–241.

Mikawa, T., Fischman, D. A., Dougherty, J. P. and Brown, A. M. C. In vivo analysis of a new lacZ retrovirus vector suitable for lineage marking in avian and other species. Exp. Cell Res. 195: 516–523.

Miller, A. D. 1990. Progress toward human gene therapy. Blood 76(2) 271–278.

Mims, C. A. 1986. Virus receptors and cell tropism. J. Infect. 12:199–204.

Ott, D., and Rein, A. 1992. Basis for receptor specificity of nonecoptropic murine leukemia virus surface glycoprotein gp70SU. J. Virol. 66:4632–4638.

Riley, S. C., Connors, S. J., Klinman, N. R., and Ogata, R. T. 1986. Preferential expression of variable region heavy chain gene segments by predominant 2,4-dinitrophenyl-specific BALB/c neonatal antibody clonotypes. Proc. Natl. Acad. Sci. 83:2589–2593. Rolt, L. 1988. In "Essential Immunology". Blackwell Scientific Publications.

Sheay, W., Nelson, S., Martinez, I., Chu, T. H. T., Bathia, S. and Dornburg, R. 1993. Downstream insertion of the adenovirus tripartite leader sequence enhances expression in universal eucaryotic vectors. Biotechniques. 15:856–861.

Shinnick, T. M., Lerner, R. A. ad Sutcliffe, J. G. 1981. Nucleotide sequence of Moloney murine leukemia virus. Nature 293:543–548.

Temin, H. M. 1986. Retrovirus vectors for gene transfer: efficient integration into and expression of exogenous DNA in vertebrate cell genomes, in "Gene Transfer" (R. Kucherlapatl, ed.) Plenum Press, New York.

Varmus, H. E. and Brown, P. 1988 Retroviruses, in "Mobile DNA" (M. Howe and D. Berg, eds.) ASM, Washington, D.C.

Watanabe, S. and Temin, H. M. 1983. Construction of a helper cell line for avian reticulonendotheliosis virus cloning vectors. Mol. Cell. Biol. 3, 2241–2249.

Weiss, R., Teich, N., Varmus, H. and Coffin, J. 1985. RNA tumor viruses. Cold Spring Harbor Laboratory, Cold Spring Harbor, N.Y.

Whitlow, M. and Filpula, D., Single-chain Fv proteins and their fusion proteins. Methods: A comparison to methods in Enzymology. Vol. 2 pp. 1–9.

Throughout this application, various publications have been referenced. The disclosures in these publications are incorporated herein by reference in order to more fully describe the state of the art.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of infecting a cell having a selected antigen, the method comprising:
    (a) producing a retroviral vector particle comprising a retroviral vector having an envelope protein wherein a viral receptor portion is at least partially defined by a single chain antibody and said viral receptor portion binds to said selected antigen; and
    (b) contacting said retroviral vector particle with the cell such that said retroviral vector particle or a portion thereof is internalized into the cell;
    wherein the cell having the selected antigen is infected by said retroviral vector.

2. The method of claim 1 wherein said retroviral vector is produced using a plasmid comprising a nucleotide sequence encoding a single molecule comprising a portion of an envelope protein and a portion of a single chain antibody.

3. The method of claim 2 wherein said nucleotide sequence encodes a portion of the envelope protein of Spleen Necrosis Virus.

4. The method of claim 2 wherein the plasmid is that identified in FIG. 2d as pTC5.

5. A method of infecting a target cell having a selected antigen, the method comprising:
    (a) producing a retroviral vector particle comprising a retroviral vector having a targeting peptide that comprises a single chain antibody fused to an envelope protein of said retroviral vector to form a targeting envelope; and
    (b) contacting said retroviral vector particle with the cell such that said retroviral vector particle or a portion thereof is internalized into the cell;
    wherein the cell having the selected antigen is infected by said retroviral vector.

6. The method of claim 5 wherein said retroviral vector particle is spleen necrosis virus.

7. The method according to claim 5 wherein the single chain antibody recognizes the hapten dinitrophenol (anti-DNP-scFv).

8. The method according to claim 5 wherein the single chain antibody comprises an antigen binding site directed against a cell-surface protein of the target cell.

9. The method according to claim 5 wherein the retroviral vector comprises a targeting envelope and a wild-type envelope.

10. A cell type specific method for introducing genes into vertebrate cells using retroviral vectors which comprises administering to the cells a retroviral vector particle having target cell specificity which comprises a retroviral vector having an antigen binding site of an antibody fused to the envelope protein of the retroviral vector, wherein the antigen binding site of the antibody replaces the natural viral receptor binding site.

11. The method according to claim 10 wherein the retroviral particle is spleen necrosis virus.

12. The method according to claim 10 wherein the antibody is a single chain antibody against the hapten dinitrophenol.

13. The method according to claim 10 wherein the antigen binding site is directed against a cell-surface protein of the target cell.

14. The method according to claim 10 wherein the retroviral vector comprises a targeting envelope and a wild-type envelope.

15. The method according to claim 14 wherein the wild type envelope is derived from spleen necrosis virus.

* * * * *